US00PP10886P

United States Patent [19]

Bergman

[11] Patent Number: Plant 10,88(

[45] Date of Patent: May 11, 199

[54] HIBISCUS PLANT NAMED 'TROPICAL BREEZE'

[75] Inventor: Wendy R. Bergman, Lehigh Acres, Fla.

[73] Assignee: Yoder Brothers, Inc., Barberton, Ohio

[21] Appl. No.: 08/995,354

[22] Filed: Dec. 29, 1997

[51] Int. Cl.[6] ..... A01H 5/00

[52] U.S. Cl. ..... Plt./67.8

[58] Field of Search ..... Plt./67.8

[56] References Cited

PUBLICATIONS

Usher. The Wordsworth Dictionary of Botany. Wordsworl Editions Ltd., Ware, p. 274, 1966.

*Primary Examiner*—Elizabeth Kemmerer

*Attorney, Agent, or Firm*—C. A. Whealy

[57] ABSTRACT

A new and distinct cultivar of Hibiscus plant named 'Tropical Breeze', characterized by its dark green leaves; uprigh and outwardly spreading, uniform and symmetrical plan habit that is appropriate for container production; florifer-ousness with numerous dark pink-colored flowers with dark red throats; good resistance to flower bud abscission; and excellent postproduction longevity.

1 Drawing Sheet

The present invention relates to a new and distinct cultivar of Hibiscus, botanically known as *Hibiscus rosa-sinensis*, and hereinafter referred to by the cultivar name Tropical Breeze.

The new cultivar is a product of a planned breeding program conducted by the inventor in Alva, Fla. The objective of the breeding program is to create new Hibiscus cultivars having uniform and compact plant habits appropriate for container production, early and uniform flowering, numerous flowers per lateral branch, desirable flower color, resistance to flower bud abscission, and good postproduction longevity.

The new cultivar originated from a cross made by the inventor in Alva, Fla., of the *Hibiscus rosa-sinensis* cultivar Tangerine (disclosed in U.S. Plant Pat. No. 8,166) as the female, or seed, parent with the *Hibiscus rosa-sinensis* cultivar Waikiki (disclosed in U.S. Plant Pat. No. 7,834) as the male, or pollen, parent. The cultivar Tropical Breeze was discovered and selected by the inventor as a flowering plant within the progeny of the stated cross in a controlled environment in Alva, Fla., on Jun. 6, 1994.

Compared to plants of the female parent, the cultivar Tangerine, plants of the new Hibiscus are more compact, flower about four days later, have slightly smaller flowers and differ in flower color. Plants of the new Hibiscus are much more compact, have lobed foliage, flower about 10 days earlier, and have a slightly darker flower color than plants of the male parent, the cultivar Waikiki.

Asexual reproduction of the new cultivar by terminal cuttings taken in a controlled environment in Alva, Fla., has shown that the unique features of this new Hibiscus are stable and reproduced true to type in successive generations.

The cultivar Tropical Breeze has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Tropical Breeze'. These characteristics in combination distinguish 'Tropical Breeze' as a new and distinct cultivar:

1. Dark green leaves.
2. Upright and outwardly spreading, uniform and symmetrical plant habit that is appropriate for container production.
3. Freely flowering, numerous dark pink-colored flowers with dark red throats.

4. Good resistance to flower bud abscission.
5. Excellent postproduction longevity.

Plants of the new Hibiscus can be compared to plants of the nonpatented cultivar Pink Versicolor. However, in side-by-side comparisons conducted in Alva, Fla., plants of the new cultivar differ from plants of the cultivar Pink Versicolor in the following characteristics:

1. Plants of the new Hibiscus are more compact than plants of the cultivar Pink Versicolor.
2. Leaves of plants of the new Hibiscus are more deeply lobed than leaves of plants of the cultivar Pink Versicolor.
3. Plants of the new Hibiscus are more floriferous than plants of the cultivar Pink Versicolor.
4. Plants of the new Hibiscus flower about 4 days earlier than plants of the cultivar Pink Versicolor.
5. Flowers of plants of the new Hibiscus are smaller than flowers of plants of the cultivar Pink Versicolor.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of typical plant of 'Tropical Breeze'.

The photograph at the bottom of the sheet comprises a close-up view of a typical flower of the 'Tropical Breeze'.

Flower and foliage colors in the photographs may appear different from the actual colors due to light reflectance.

DETAILED BOTANICAL DESCRIPTION

The following observations, measurements and values describe plants grown in Alva, Fla., and Keller, Tex., in 28-cm containers during the summer and early autumn with day temperatures ranging from 16 to 35° C. and night temperatures ranging from 10 to 24° C. In the description, color references are made to The Royal Horticultural Society Colour Chart except where general terms of ordinary dictionary significance are used.

Botanical classification: *Hibiscus rosa-sinensis* cultivar Tropical Breeze.

Parentage:

*Female or seed parent.*—*Hibiscus rosa-sinensis* cultivar Tangerine, disclosed in U.S. Plant Pat. No. 8,166.

*Male or pollen parent.*—*Hibiscus rosa-sinensis* cultivar Waikiki, disclosed in U.S. Plant Pat. No. 7,834.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorous, thick and well-branched.

Plant description:

*Plant form and growth habit.*—Perennial, evergreen, upright to outwardly spreading, inverted triangle, uniform and symmetrical plant habit. Moderate vigor.

*Branching habit.*—Freely branching, usually about five lateral branches develop after removal of terminal apex.

*Plant height, soil level to top of flowers.*—About 37 cm.

*Plant diameter, area of spread.*—About 48 cm.

*Lateral branch description.*—Length: About 24 cm. Diameter: About 1 cm. Texture: Immature, smooth; woody with age.

*Color.*—Immature: Close to 200A. Mature: Grayish green.

Foliage description:

*Arrangement.*—Alternate, single.

*Length.*—About 10.5 cm.

*Width.*—About 9 cm.

*Shape.*—Ovate.

*Apex.*—Acute to acuminate.

*Base.*—Cordate to obtuse.

*Margin.*—Crenate, fully mature leaves lobed.

*Texture.*—Glabrous and glossy/shiny on both surfaces.

*Color.*—Young foliage, upper surface: Darker and greener than 146A. Young foliage, lower surface: Greener than 146A. Mature foliage, upper surface: Dark green, darker than 147A. Mature foliage, lower surface: Greener than 146A.

*Petiole.*—Length: About 5 cm. Diameter: About 4 mm. Texture: Smooth or with very fine pubescence on upper surface. Color: Close to 200A.

Flower description:

*Natural flowering season.*—Usually spring and summer or during periods of warm weather.

*Flower arrangement.*—Flowers arranged singly at terminal leaf axils. Freely flowering with usually four to five flower buds and/or open flowers per terminal apex. Flowers flat and face upright and outward.

*Flower appearance.*—Star-shaped single. Dark pink-colored petals with dark red throat. Flowers are open for about one day before closing. Flowers self-cleaning.

*Flower diameter.*—About 11 cm.

*Flower bud (just before showing color).*—Rate of opening: About one day depending on temperatures. Length: About 2.2 cm. Diameter: About 1 cm. Shape: Columnar, oblong.

*Petals.*—Texture: Crepe, smooth. Arrangement: Corolla consists of five petals that overlap. Shape: Spatulate with rounded apex. Margin: Entire. Length: About 6.75 cm. Width: About 5.25 cm. Color: Upper surface: 54A/54B with slightly darker veins. Lower surface: 54B with 54A veins. Yellowish, 11A, at right edges of petals. Throat: Dark red, 46A/53A.

*Sepals.*—Appearance: Six sepals fused into a star-shaped calyx. Shape: Linear. Texture: Smooth. Color, outer surface: 144A.

*Peduncles.*—Length: About 4.5 cm. Diameter: About 3 mm at apex. Angle: Upright. Strength: Strong, rigid. Color: 148A with brown overtones towards base.

*Reproductive organs.*—Androecium: Stamen number: Numerous. Stamen length: About 5 mm. Anther shape: Globular. Anther size: About 1 mm. Amount of pollen: Abundant. Pollen color: 21A. Gynoecium: Pistil length: About 6.75 cm. Style color: Apex: 51B. Base: 46A to 47A. Stigma number: Five. Stigma shape: Round. Stigma diameter: About 3 mm. Stigma color: 46A. Ovary color: Light green, 154B.

Disease resistance: No known Hibiscus diseases observed to date on plants grown under commercial greenhouse conditions.

Seed production: If cross-pollinated, seed production may be observed. Usually one to twenty seeds per capsule.

It is claimed:

1. A new and distinct Hibiscus plant named 'Tropical Breeze', as illustrated and described.

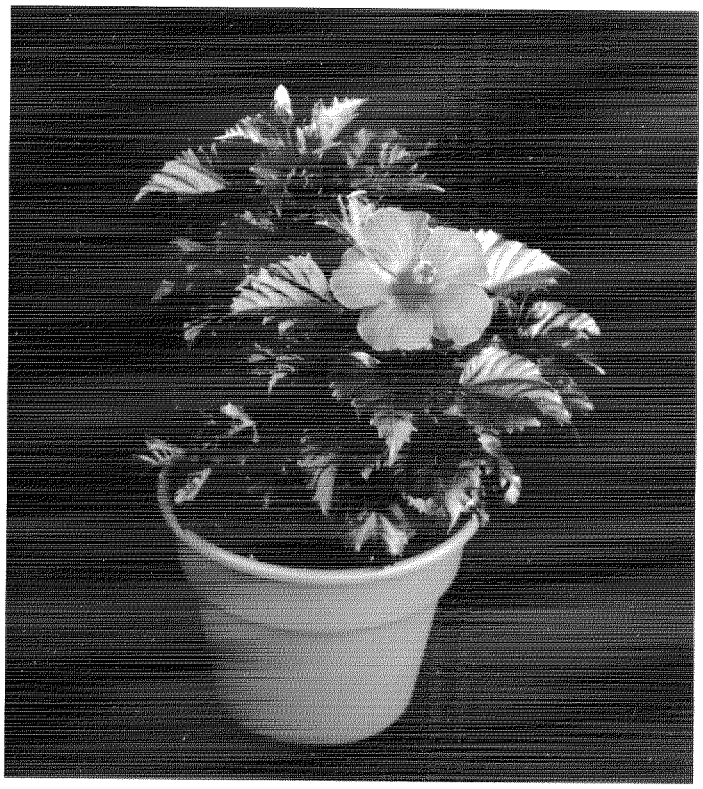
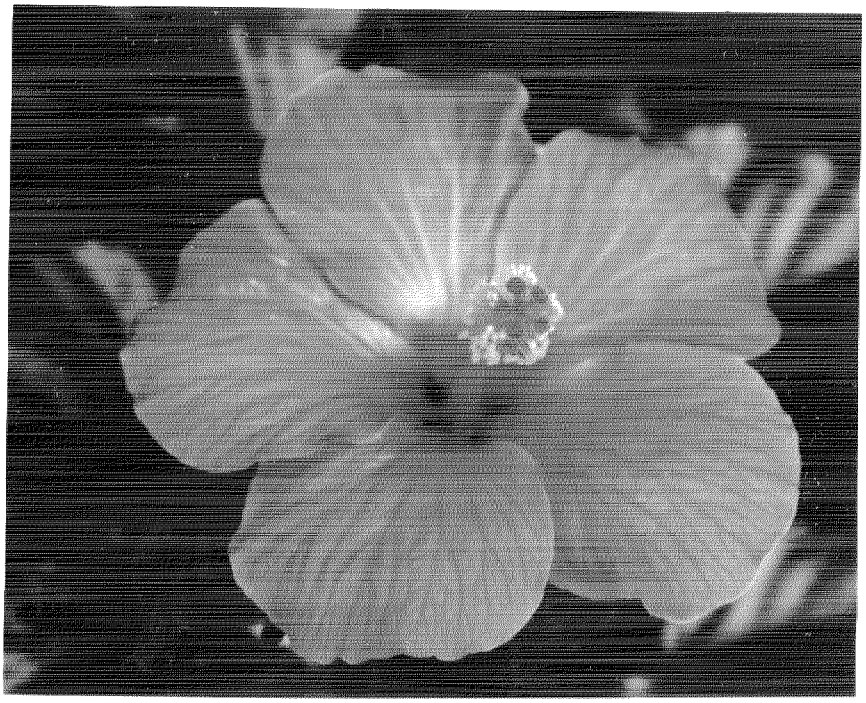

* * * * *